(12) United States Patent
Miller

(10) Patent No.: US 11,606,951 B1
(45) Date of Patent: Mar. 21, 2023

(54) ORGAN PRESERVATION SYSTEM

(71) Applicant: Malleaka Oris Miller, Mebane, NC (US)

(72) Inventor: Malleaka Oris Miller, Mebane, NC (US)

( * ) Notice: Subject to any disclaimer, the term of this patent is extended or adjusted under 35 U.S.C. 154(b) by 108 days.

(21) Appl. No.: 17/247,988

(22) Filed: Jan. 4, 2021

Related U.S. Application Data

(60) Provisional application No. 62/956,504, filed on Jan. 2, 2020.

(51) Int. Cl.
*A01N 1/02* (2006.01)

(52) U.S. Cl.
CPC .................. *A01N 1/0242* (2013.01)

(58) Field of Classification Search
CPC ............... A01N 1/0242; A01N 1/0252; A61F 2007/002; A61F 2007/101
See application file for complete search history.

(56) References Cited

U.S. PATENT DOCUMENTS

| | | | | |
|---|---|---|---|---|
| 3,091,242 A | * | 5/1963 | Johnson, Jr. | A61M 19/00 607/105 |
| 5,005,374 A | * | 4/1991 | Spitler | F25D 3/08 383/110 |
| 5,150,706 A | * | 9/1992 | Cox | A61F 7/10 604/113 |

FOREIGN PATENT DOCUMENTS

WO    WO-0057783 A1 * 10/2000 ............. G01V 15/00

* cited by examiner

*Primary Examiner* — William H. Beisner
(74) *Attorney, Agent, or Firm* — Dunlap Bennett & Ludwig, PLLC

(57) ABSTRACT

An organ preservation system is provided. The organ preservation system is embodied in a sleeve adapted to maintain a pre-transplant organ at a temperature lower than ambient temperature through a plurality of bladders interconnected by a deformable mesh. With the organ in the sleeve, each vessel of the organ can pass through separate, deformable holes of the mesh, facilitating ease of identification of each vessel needed for the pending vascular anastomosis.

9 Claims, 7 Drawing Sheets

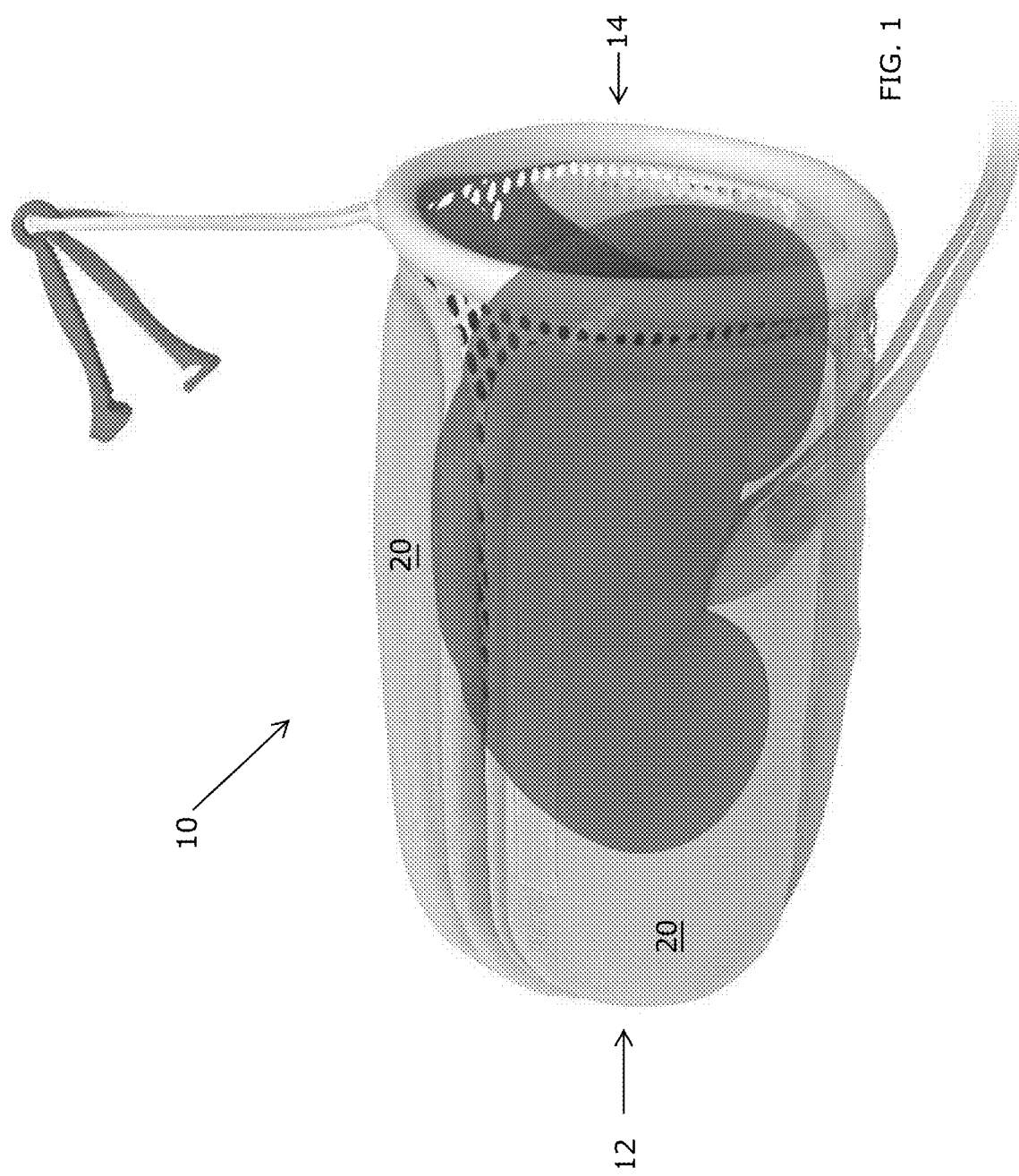

ORGAN PRESERVATION SYSTEM

CROSS-REFERENCE TO RELATED APPLICATION

This application claims the benefit of priority of U.S. provisional applications: No. 62/956,504 filed 2 Jan. 2020, the contents of which are herein incorporated by reference.

BACKGROUND OF THE INVENTION

The present invention relates to medical devices and, more particularly, an organ preservation system that embodies a sleeve that houses an organ during transplantation anastomosis and keeping the temperature of the organ cooler than the ambient temperature.

A vascular anastomosis is a surgical procedure that is used to connect vessels to each other. Surgery is generally a time sensitive activity and being pushed for time when creating the vascular anastomoses in a kidney transplantation is associated with inferior transplant outcome. In short, extended anastomosis times affect transplanted organ graft success.

Additionally, historically during organ transplant anastomosis the organ is at room temperature or slightly warmer as a result of having to sit under the operating room lights. Organ cell death happens as a result of warm ischemic time (no blood flow to the organ and the organ not being in a cooled protective environment).

Currently, many surgeons use a Raytec™ sponge and cut a hole out for vessel access. This makeshift approach, however, risks the possibility of retaining a portion of the cut sponge in the patient when the associated organ is transplanted, and the makeshift approach does not address the warm ischemic time of the organ.

As can be seen, there is a need for an organ preservation system adapted to house the organ during transplantation anastomosis in such a way as to decrease the anastomosis time, decrease the risk to the patient of retaining foreign bodies, and enabling cooling of the organ. The organ preservation system embodies a sleeve that facilitates optimal positioning of the housed organ during anastomosis, provides a small section of stretch mesh to allow for adequate exposure of vessels and a cooled environment conducive of less/minimal cell death and as a result overall better graft function post-operatively. The sleeve is further adapted to provide adequate separation of vessels and thus increased speed of sequential anastomoses. As a result, the sleeve will allow for ease of access to the vessels as well as eliminate the possibility of retaining a portion of the housing device in the patient.

SUMMARY OF THE INVENTION

In one aspect of the present invention, an organ preservation system includes the following: a sleeve defined by a plurality of bladders interconnected by a deformable mesh, whereby a vessel of an organ housed in the sleeve can be retained in separate, deformable holes, facilitating identification of each vessel, wherein each bladder has a cavity, whereby a temperature preservation solution (including cold saline solution or temperature-related solutions consistent with the disclosure herein) retainable in the cavity, wherein the sleeve extends between a closed posterior end and an open anterior end, wherein a periphery defines an opening of the open anterior end; and wherein a closure is operatively associated with the periphery to move the opening from an open condition to a closed condition, wherein the closure and the deformable mesh are X-ray detectable; and in certain embodiments further including one or more Luer connectors disposed along an exterior surface of the plurality of bladders.

These and other features, aspects and advantages of the present invention will become better understood with reference to the following drawings, description and claims.

BRIEF DESCRIPTION OF THE DRAWINGS

FIG. 1 is a perspective view of an exemplary embodiment of the present invention;

DETAILED DESCRIPTION OF THE INVENTION

Figure 3:
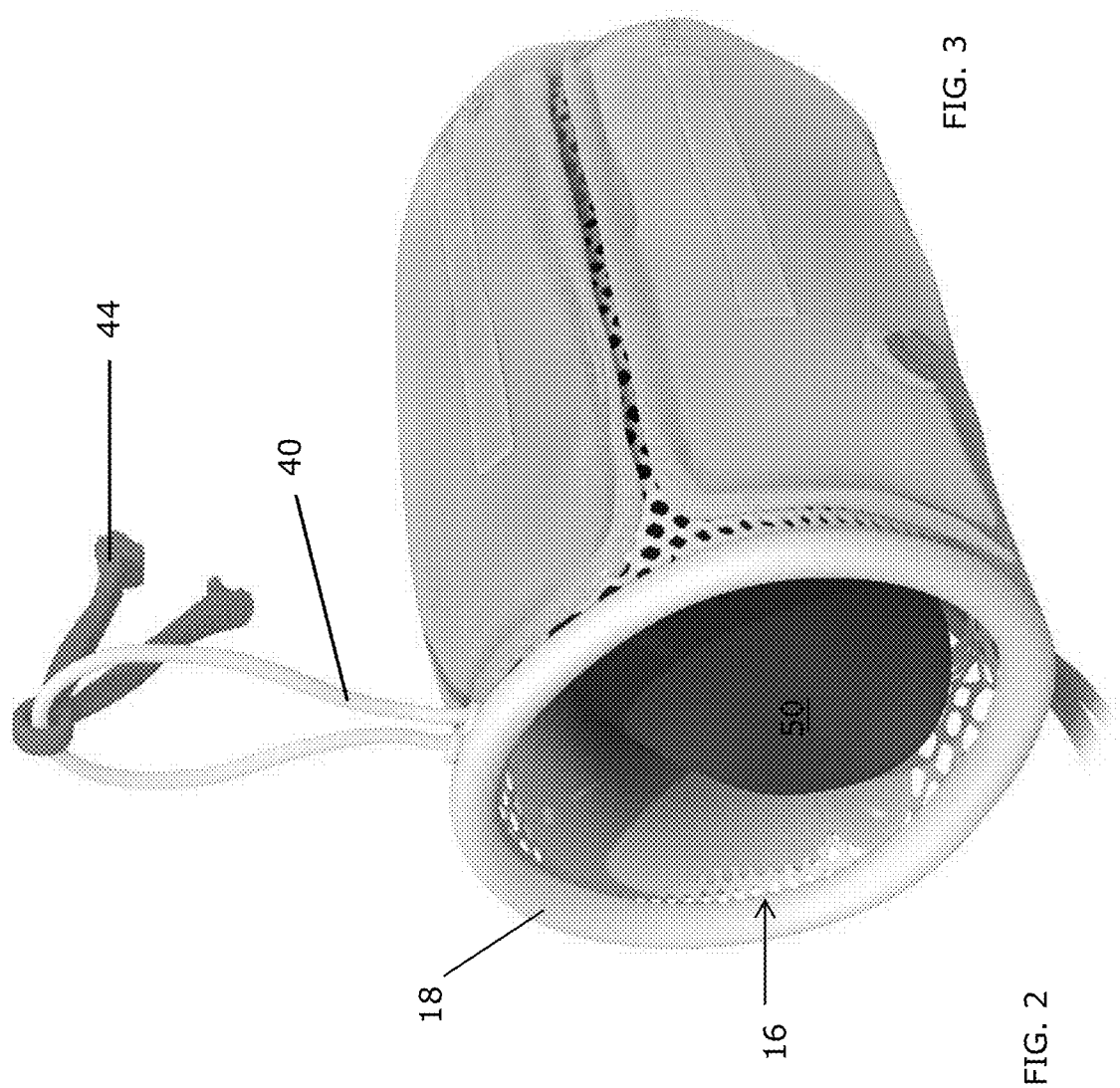
FIG. 3 is a perspective view of an exemplary embodiment of the present invention, illustrating an open condition.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides an organ preservation system. The organ preservation system is embodied in a sleeve adapted to maintain a pre-transplant organ at a temperature lower than ambient temperature through a plurality of bladders interconnected by a deformable mesh material. With the organ in the sleeve, each vessel of the organ can pass through separate, deformable holes of the mesh, facilitating ease of identification of each vessel needed for the pending vascular anastomosis.

Referring now to FIGS. 1 through 8, the present invention may include a sleeve 10 dimensioned and adapted to house an organ 50 during transplantation anastomosis. The sleeve 10 may have a closed posterior end 12 and an open anterior end 14. The opening 16 of the anterior end 14 is defined by a periphery 18. The sleeve 10 may be comprise hypoallergenic and non-latex material.

The sleeve 10 may include one or more absorbent pads or bladders 20. Each bladder may be covered in a medical dress type covering, such as but not limited to Tegaderm™. A stretchable mesh 30 may interconnect the one or more absorbent pads or bladders 20 and the periphery 18. The medical dressing covered absorbent pad/bladder 20 can be used to absorb temperature, such as from cold preservation solution (saline) or the like, thus keeping the organ 50 at cool temperatures thereby improving graft success outcomes. The interior aspect of the sleeve 10 (where the bladders 20 will be in contact with the organ 50) will be hydrophilic and/or have a liner to protect the organ's surface from any friction damage.

The stretchable mesh 30 may include X-ray detectable material. The mesh portion 30 can be made of regular stretch net or can also be made of a specialized dissolvable material/film that can be impregnated with hemostatic and/or antibiotic agents. The stretch mesh fabric 30 allows for ease of separation, access, and sequential anastomoses of vessels needed during transplantation thus decreasing ischemic time (i.e., the time blood supply to tissues is restricted) and increasing graft success.

Figure 2:
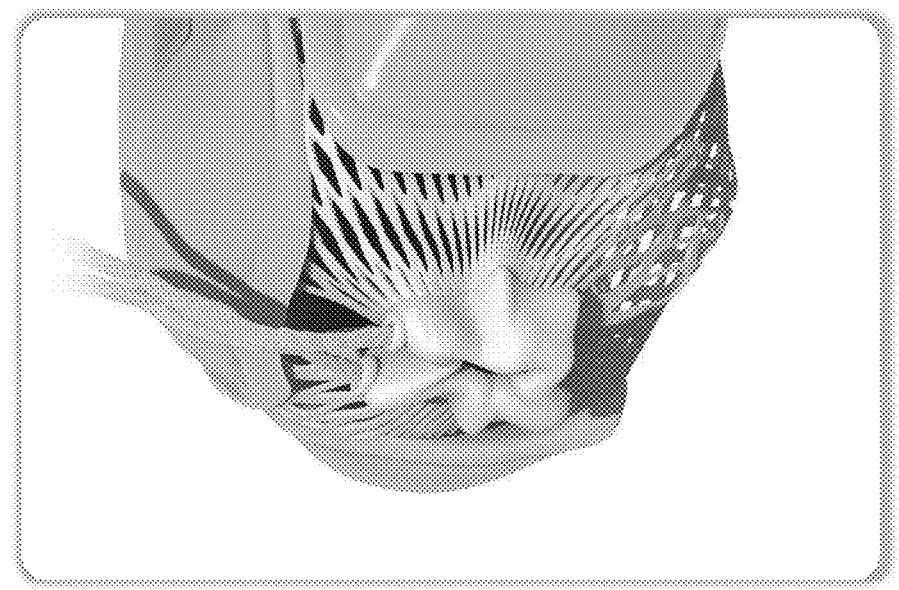
FIG. 2 is a detailed perspective view of an exemplary embodiment of the present invention, illustrating a closed condition.
Figure 4:
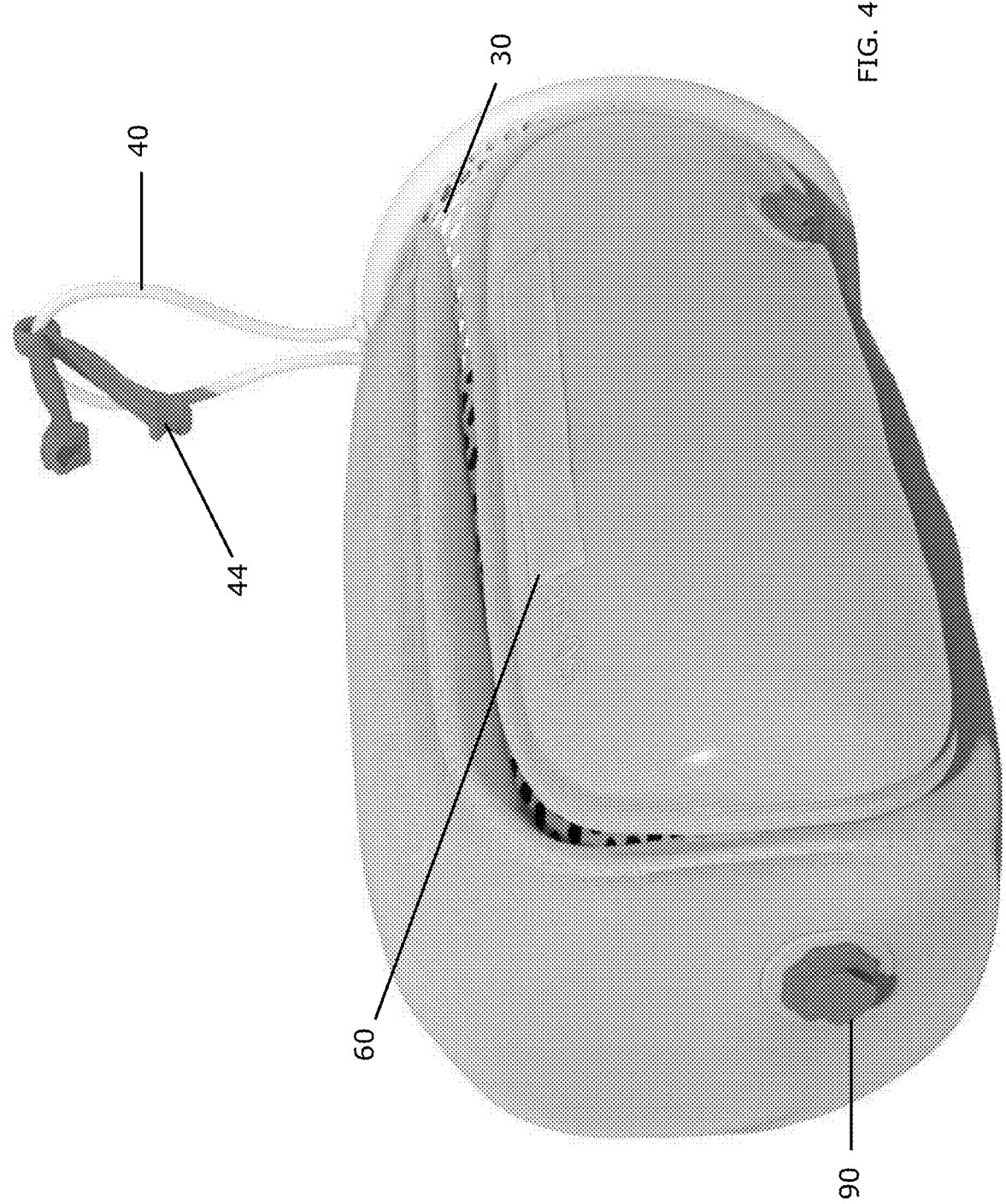
FIG. 4 is a perspective view of an exemplary embodiment of the present invention.
Figure 5:
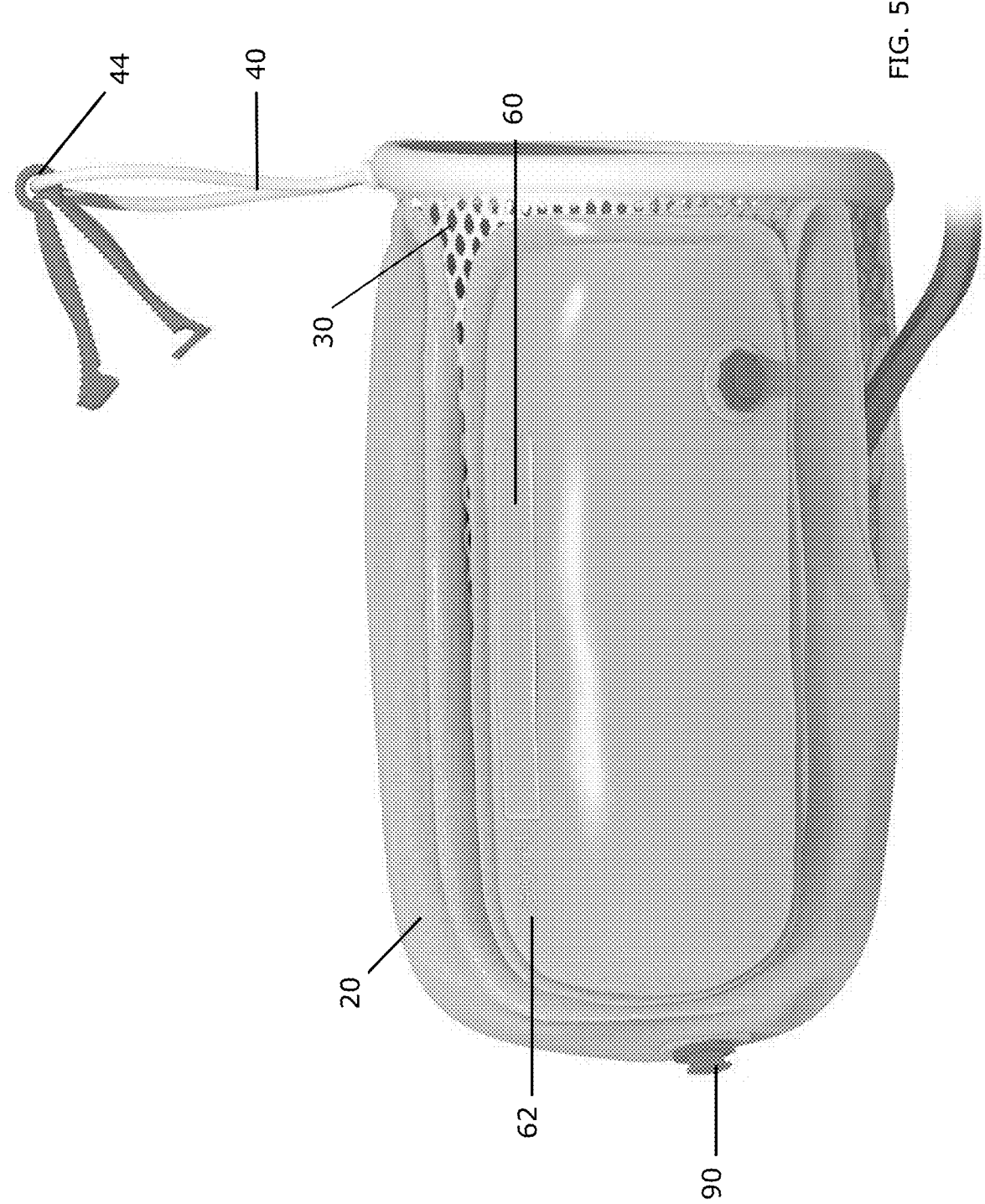
FIG. 5 is a lateral elevation view of an exemplary embodiment of the present invention.
Figure 6:
FIG. 6 is a top plan view of an exemplary embodiment of the present invention.

A filament closure 40 may be operatively associated with the periphery 18 for selectively moving the anterior end opening between an open condition and a closed condition. The filament closure 40 may include X-ray detectable material. A fastener 44, such as a tie or clasp, may be attached on the anterior side of the sleeve 10 or the filament closure 40, enabling formation of a locked engagement in the closed condition. The filament closure 40 may enable the closed condition to be the cinching of the periphery 18, purse-string fashion, as illustrated in FIG. 2. The closed condition secured the housed organ 50 in the sleeve 10, providing protection until transplanted. The fastener 44 will allow the surgeon to tie or attach the sleeve to their retractor system or drapes (not shown) allowing for safe, secure positioning during anastomosis.

Figure 7:
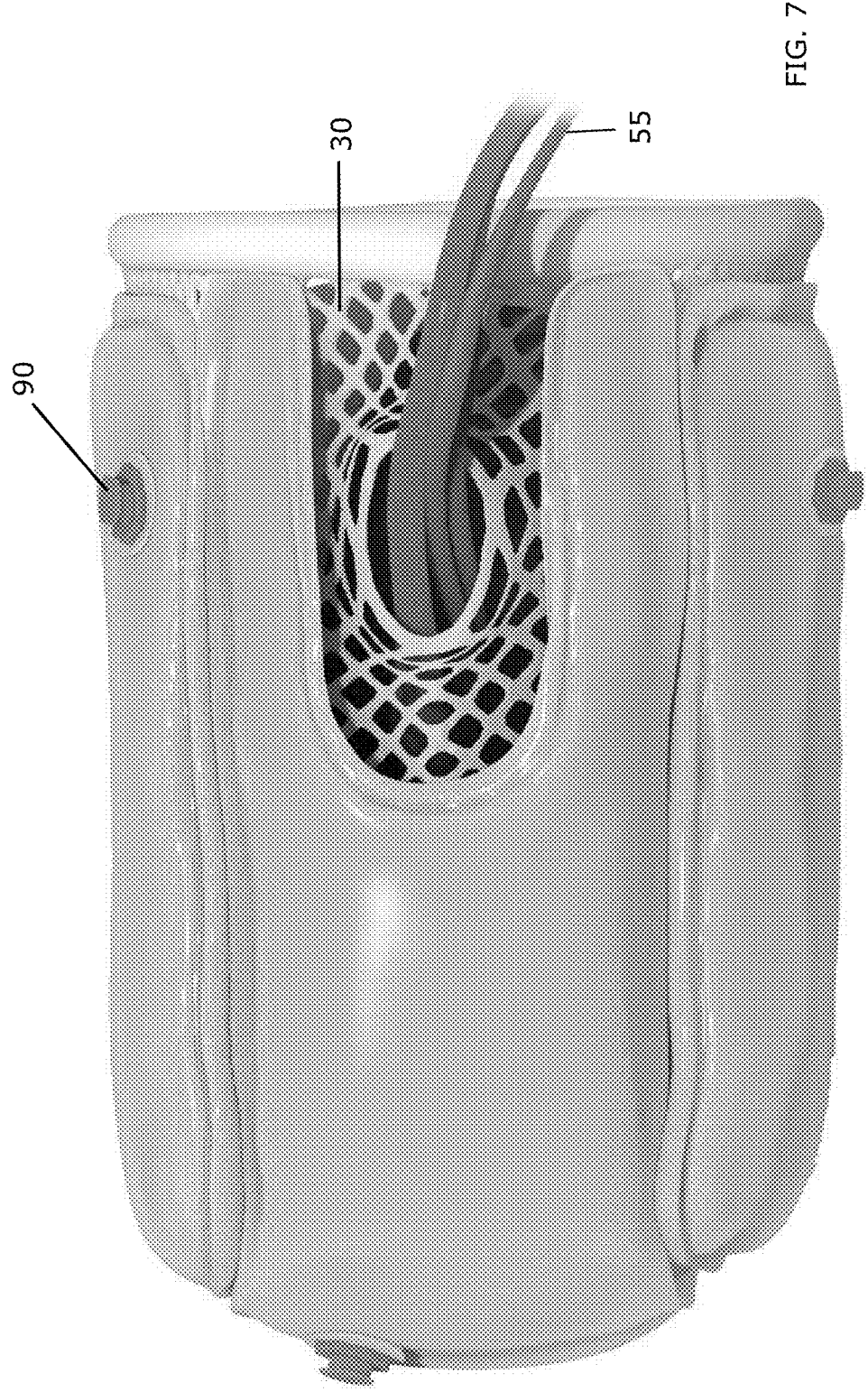
FIG. 7 is a bottom plan view of an exemplary embodiment of the present invention.
Figure 8:
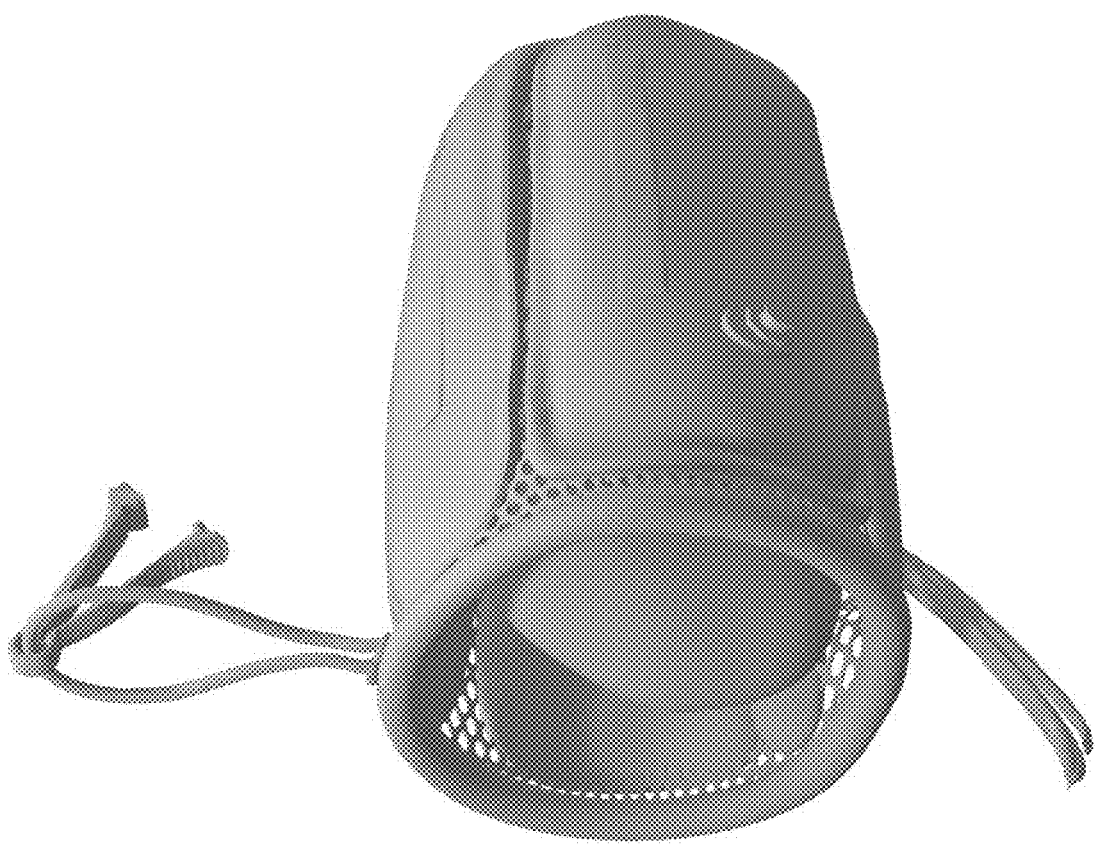
FIG. 8 is a perspective view of an exemplary embodiment of the present invention.

The organ sleeve 10 may be oriented with the plastically deformable mesh fabric 30 facing the floor and the anterior end 14 oriented toward a first direction above the patient. The organ 50 would be carefully placed into the sleeve 10 with vessels 55 facing down toward the stretch net fabric 30. Vessels 55 may be separated into individual holes of the mesh 30 and pulled through allowing for ease of identification, access, and speed during anastomosis. Additionally, the stretchability of the mesh fabric 30 allows a practitioner to stretch each hole into a plastically deformed, larger hole, as illustrated in FIG. 7. The periphery 18 may be cinched closed and secured allowing for a safe, padded, cold temperature location for the organ during anastomosis. The organ sleeve 10 may then be secured to the retractor system by either the filament closure 40 and/or fastener 44 allowing for a secure location for the organ while anastomosis is occurring. The vessels 55 which were pulled through the stretch net fabric 30 may be facing down toward the recipient's body near the anastomosis location.

These sleeve components combined will allow for safety of the organ 50 prior to anastomosis, optimal positioning of the organ 50 during anastomosis, and increased speed of anastomosis by way of easy identification and visualization. This all results in decreased cold ischemic time for the organ graft and increased positive outcomes for the recipients.

Some surgeons may want to tie the sleeve 10 to the retractor system. A specialized type of padding with cold temperature regulation would make the present invention better as the organ temperature could be closely monitored, such as through sensors operatively associated with temperature indicator 60 as well as a volume indicator 62 disposed along an external surface of one of the pads/bladders 20.

Likewise, Luer connectors 90 may be provided along the bladders 20, where syringes can be securely attached and where cold saline fused.

The stretch net fabric 30 location can be shuffled around as well as the size of the bladders 20 and thus overall sleeve 10 can be modified. The basic model of the sleeve 10 can be modified for any organ type depending on the type of access needed for the vessel anastomosis.

In a provisional embodiment, the present invention may include an organ sleeve 10 having a slit along the anterior/top portion thereof, creating a pocket on both sides for regulating of the temperature of the organ it holds, for instance a kidney. Each pocket may accommodate one kidney/oval shaped cooling element, such as ice packs, to be placed on either/both sides of the kidney (for a total of two ice packs to be used in combination with the sleeve). These cooling elements will keep the kidney cool during anastomosis. The placement of the cooling elements in the pockets on either side of the kidney within the organ sleeve will allow for a barrier between the cooling pack and the kidney thus protecting the outer layer of the kidney from any injury related to the cold ice pack.

In other embodiments, the sleeve may include three (3) bladders separated by stretch mesh (to accommodate different sized organs), where there are two (2) lateral bladders (one per side) running along the lateral aspects of the sleeve. There is also one long wrap around bladder which runs from the anterior aspect and wraps around to the posterior aspect of the sleeve. Along the posterior aspect, the wrap around bladder may be separated by a small section of stretch mesh which will be used to accommodate the organ vessels. Each bladder may be made of a hypo-allergenic, nonlatex material. Each bladder may have a low-profile Luer-lock mechanism 90 to allow for infusion of cold fluids. Each bladder will be labeled with max fluid content as well as a temperature indicator.

The interior of the sleeve will either have a hydrophilic lining throughout or each bladder will be hydrophilic in nature along the medial aspects (the area touching the organ) to aid in preventing damage to the organ surface from contact with the bladder. These bladders and stretch net can be modified/shuffled in order to accommodate different organs for transplant and or use during surgery where time is of the essence during anastomosis. The sleeve has a purse string type closure at the open end and a clamp attached to the radiopaque filament used for the purse string closure. The clamp is used for attaching to the surgical drapes allowing for optimization of location during anastomosis. The stretch net on the posterior aspect continue to allow for accommodation of the sequential anastomosis. The combination of the sequential anastomosis (more timely) with the cool environment (minimizing cell death) will greatly improve the organ function and life of organ transplant patients.

A method of using the present invention may include the following. The sleeve 10 disclosed above may be provided. Each bladder 20 will be filled with the appropriate/recommended amount of specified cold solution. The organ 50 will be placed in the sleeve 10 through the opening 16, wherein the sleeve 10 is oriented with the mesh 30 facing downward toward the patient and the open end facing the laterality of the organ to be transplanted.

The vessels 55 will be pulled through the stretch net on the posterior end of the sleeve. The purse-string closure of the periphery 18 effectuates the closed condition, wherein the organ 50 can be cooled, effectively reducing cell death related to warm ischemic time and vessels are visualized easily for sequential anastomosis. Once anastomosis has completed and it is time for removal of the sleeve, the surgeon simply needs to cut the stretch mesh 30 on the posterior aspect from the hole vessels were pulled through toward the purse string closure. The surgeon is to continue cutting through the purse string closure for complete clearance.

In certain embodiments, the sleeve 1 can be secured to a retractor system by connecting the filament closure 40 or the fastener 44 to the retractor system or using the included fastener. Once the organ 50 is secured to the retractor system, the surgeon can begin anastomosis. To remove the sleeve 10, a user would cut the stretch net fabric 30 away along the indicated blue line. The sleeve 10 is now detached from the organ 50 and the sleeve 10 can be discarded.

It should be understood, of course, that the foregoing relates to exemplary embodiments of the invention and that modifications may be made without departing from the spirit and scope of the invention as set forth in the following claims.

What is claimed is:

1. An organ preservation system, comprising:
    a sleeve defined by a plurality of bladders interconnected by a deformable mesh; and
    the mesh comprises a plurality of holes between adjacent bladders of the plurality of bladders, wherein each hole is plastically deformable so an area thereof is plastically deformed larger, whereby each vessel of an organ housed in the sleeve can be retained in separate plastically deformable hole, facilitating identification of each vessel.

2. The organ preservation system of claim 1, wherein each bladder has a cavity, whereby a temperature preservation solution is retainable in the cavity.

3. The organ preservation system of claim 2, wherein the sleeve extends between a closed posterior end and an open anterior end.

4. The organ preservation system of claim 3, wherein a periphery defines an opening of the open anterior end; and wherein a closure is operatively associated with the periphery to move the opening from an open condition to a closed condition.

5. The organ preservation system of claim 4, wherein the closure and the deformable mesh are X-ray detectable.

6. The organ preservation system of claim 5, further comprising one or more Luer connectors disposed along an exterior surface of the plurality of bladders.

7. The organ preservation system of claim 6, wherein the closed condition the periphery is cinched.

8. The organ preservation system of claim 7, wherein a perimeter of each bladder is completely circumscribed by and connected to the mesh so an interior-surface of the bladder faces a lumen of the sleeve, wherein the interior-facing surface provides a hydrophilic material for engaging the organ.

9. An organ preservation system, comprising:
    a sleeve defined by a plurality of bladders interconnected by a deformable mesh; and
    the mesh comprises a plurality of holes between adjacent bladders of the plurality of bladders, wherein each hole is deformable by a force so an area thereof is deformed permanently larger, whereby each vessel of an organ housed in the sleeve can be retained in separate deformable hole, facilitating identification of each vessel.

* * * * *